United States Patent
Ohishi

(10) Patent No.: US 10,499,871 B2
(45) Date of Patent: Dec. 10, 2019

(54) X-RAY DIAGNOSTIC APPARATUS AND IMAGE PROCESSING APPARATUS

(71) Applicant: Toshiba Medical Systems Corporation, Otawara-shi (JP)

(72) Inventor: Satoru Ohishi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1121 days.

(21) Appl. No.: 14/834,881

(22) Filed: Aug. 25, 2015

(65) Prior Publication Data

US 2016/0051218 A1 Feb. 25, 2016

Related U.S. Application Data

(63) Continuation of application No. PCT/JP2014/054957, filed on Feb. 27, 2014.

(30) Foreign Application Priority Data

Feb. 27, 2013 (JP) .................................. 2013-037984
Feb. 27, 2014 (JP) .................................. 2014-037405

(51) Int. Cl.
  *A61B 6/00* (2006.01)
  *G06T 7/32* (2017.01)
  *G06T 7/11* (2017.01)

(52) U.S. Cl.
  CPC .......... *A61B 6/5258* (2013.01); *A61B 6/4441* (2013.01); *A61B 6/481* (2013.01);
  (Continued)

(58) Field of Classification Search
  CPC ..... A61B 6/5258; A61B 6/4441; A61B 6/481; A61B 6/486; A61B 6/501; A61B 6/504;
  (Continued)

(56) References Cited

U.S. PATENT DOCUMENTS

2006/0215889 A1   9/2006   Omi et al.
2008/0009716 A1   1/2008   Ohishi
(Continued)

FOREIGN PATENT DOCUMENTS

JP   2007-325920 A   12/2007
JP   2007-330669 A   12/2007
(Continued)

OTHER PUBLICATIONS

International Search Report dated Jun. 3, 2014 for PCT/JP2014/054957 filed on Feb. 27, 2014 with English Translation.
(Continued)

*Primary Examiner* — Carolyn A Pehlke
(74) *Attorney, Agent, or Firm* — Oblon, McClelland, Maier & Neustadt, L.L.P.

(57) ABSTRACT

An X-ray diagnostic apparatus according to an embodiment includes processing circuitry. The processing circuitry is configured to measure respective profiles on contrast media concentration in regions of interest including blood vessels set at about the same position in two subtraction images of subject's head taken from about the same direction at different radiography times. The processing circuitry is configured to determine a correction factor so that the two profiles measured are approximately matched. The processing circuitry is configured to correct at least one of the two subtraction images on the basis of the correction factor determined. The processing circuitry is configured to control so as to display information based on the two subtraction images that at least one thereof has been corrected on a display.

14 Claims, 13 Drawing Sheets

(52) U.S. Cl.
CPC .............. *A61B 6/486* (2013.01); *A61B 6/501* (2013.01); *A61B 6/504* (2013.01); *A61B 6/507* (2013.01); *A61B 6/5205* (2013.01); *A61B 6/5217* (2013.01); *A61B 6/54* (2013.01); *G06T 7/11* (2017.01); *G06T 7/32* (2017.01); *A61B 6/461* (2013.01); *G06T 2207/10081* (2013.01); *G06T 2207/20224* (2013.01); *G06T 2207/30016* (2013.01); *G06T 2207/30048* (2013.01); *G06T 2207/30101* (2013.01); *G06T 2207/30104* (2013.01)

(58) Field of Classification Search
CPC ....... A61B 6/5205; A61B 6/5217; A61B 6/54; A61B 6/461; A61B 6/032; G06T 7/0012; G06T 7/11; G06T 7/32; G06T 2207/10116; G06T 5/50
See application file for complete search history.

(56) References Cited

U.S. PATENT DOCUMENTS

| | | |
|---|---|---|
| 2013/0208957 A1 | 8/2013 | Wiesner et al. |
| 2014/0003687 A1* | 1/2014 | Jou ........................ A61B 6/481 382/130 |

FOREIGN PATENT DOCUMENTS

| | | |
|---|---|---|
| JP | 2009-153870 A | 7/2009 |
| WO | WO 2004/089218 A1 | 10/2004 |
| WO | WO 2011/151752 A1 | 12/2011 |

OTHER PUBLICATIONS

Written Opinion dated Jun. 3, 2014 for corresponding application PCT/JP2014/054957 (with statement of relevancy).

* cited by examiner

FIG.11A
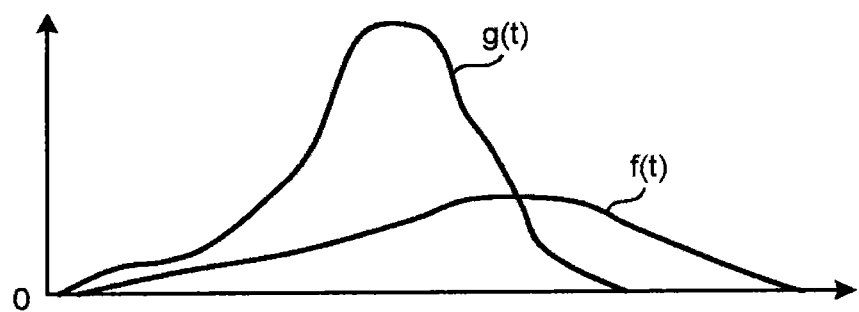
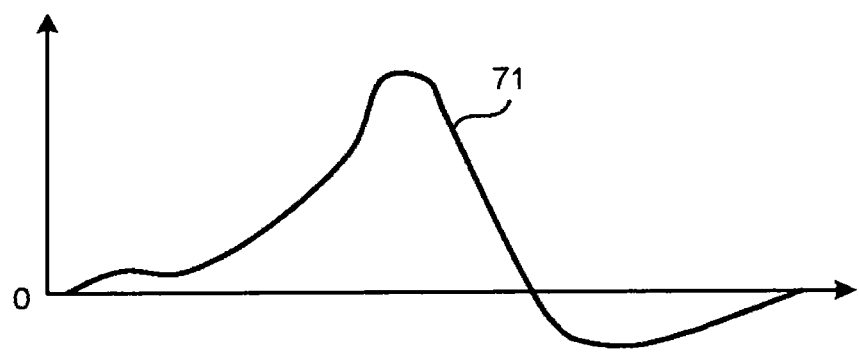
FIG. 11B

FIG. 11C
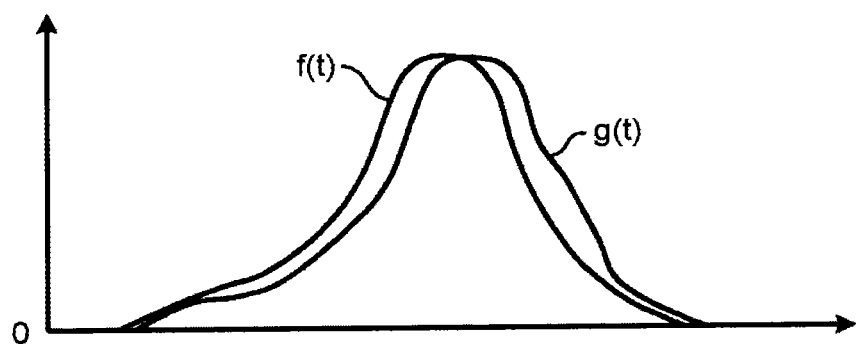
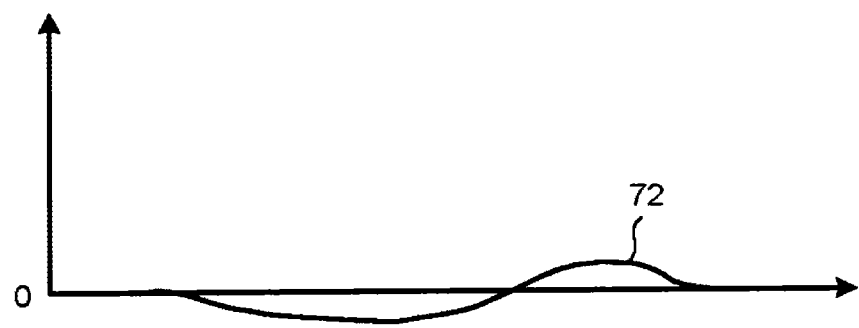
FIG. 11D

FIG. 11E
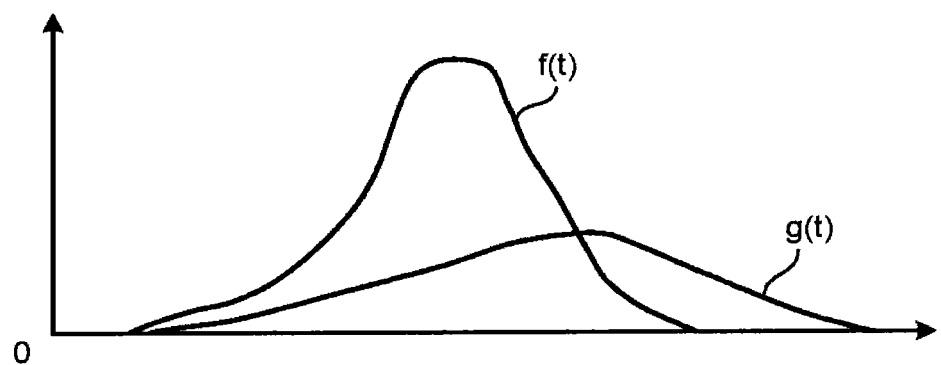
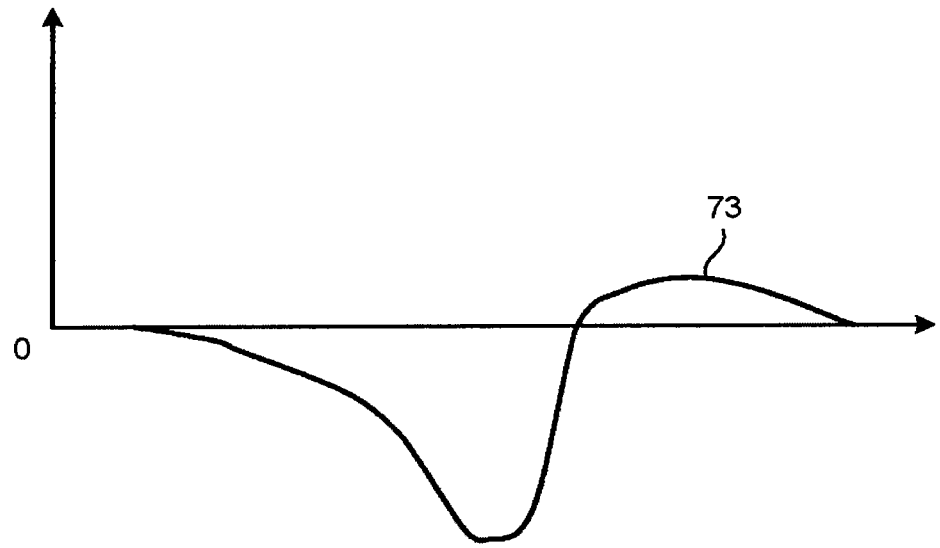
FIG. 11F

X-RAY DIAGNOSTIC APPARATUS AND IMAGE PROCESSING APPARATUS

CROSS-REFERENCE TO RELATED APPLICATIONS

This application is a continuation of PCT international application Ser. No. PCT/JP2014/054957 filed on Feb. 27, 2014 which designates the United States, incorporated herein by reference, and which claims the benefit of priority from Japanese Patent Application No. 2013-037984, filed on Feb. 27, 2013, the entire contents of which are incorporated herein by reference. The entire contents of the prior Japanese Patent Application No. 2014-037405, filed on Feb. 27, 2014, are also incorporated herein by reference.

FIELD

Embodiments described herein relate generally to an X-ray diagnostic apparatus and an image processing apparatus.

BACKGROUND

Conventionally, brain perfusion analysis is known in the diagnosis of cerebral infarction with an X-ray computed tomography (CT) apparatus. In the brain perfusion analysis, there is used a brain perfusion image that is tomograms of the brain taken through injection of a contrast media and represents the state of blood perfusion.

Furthermore, in recent years, there is known an analysis method to manually or automatically set a boundary line that divides a cross-sectional image of the head taken with an X-ray CT apparatus into two parts of the right and left hemispheres, reverse one of images divided by the boundary line and superimpose the reversed image on the other image, and create a subtraction image between the superimposed images. According to this analysis method, a lesion area stands out in the subtraction image; therefore, comparative reading of the right and left hemispheres is facilitated, and this makes it possible to check abnormal blood flow such as cerebral infarction. However, the above-described conventional technology may fail to make an accurate comparison between a preoperative image and a postoperative image.

BRIEF DESCRIPTION OF THE DRAWINGS

FIGS. 11A and 11B are an exemplary diagram illustrating an example of an analysis result displayed on the display according to the first embodiment;

FIGS. 11C and 11D are an exemplary diagram illustrating an example of an analysis result displayed on the display according to the first embodiment;

FIGS. 11E and 11F are an exemplary diagram illustrating an example of an analysis result displayed on the display according to the first embodiment.

DETAILED DESCRIPTION

According to an embodiment, an X-ray diagnostic apparatus includes processing circuitry. The processing circuitry is configured to measure respective profiles on contrast media concentration in regions of interest including blood vessels set at about the same position in two subtraction images of subject's head taken from about the same direction at different radiography times. The processing circuitry is configured to determine a correction factor so that the two profiles measured are approximately matched. The processing circuitry is configured to correct at least one of the two subtraction images on the basis of the correction factor determined. The processing circuitry is configured to control so as to display information based on the two subtraction images that at least one thereof has been corrected on a display.

Embodiments of an X-ray diagnostic apparatus and image processing apparatus will be explained in detail below on the basis of accompanying drawings. Incidentally, the embodiment is not limited by the embodiments described below.

First Embodiment

Figure 1:
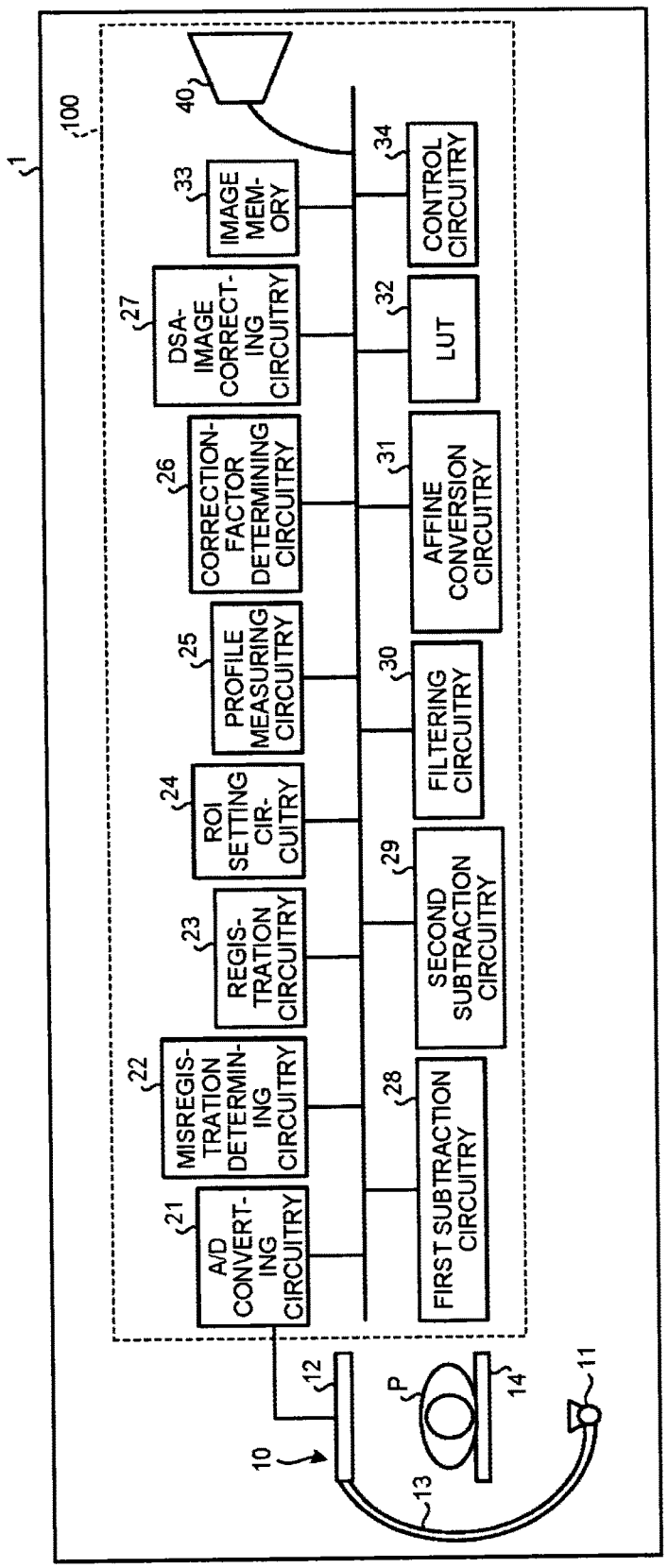
FIG. 1 is an exemplary diagram illustrating an example of a configuration of an X-ray diagnostic apparatus according to a first embodiment.

FIG. 1 is an exemplary diagram illustrating an example of a configuration of an X-ray diagnostic apparatus 1 according to a first embodiment. The X-ray diagnostic apparatus 1 according to the first embodiment comprises an X-ray mechanism 10 and an image processing apparatus 100. The X-ray mechanism 10 comprises an X-ray tube 11, a flat panel detector (FPD) 12, a C-shaped arm 13, and a bed 14. The C-shaped arm 13 supports the X-ray tube 11 and the FPD 12, and is rotated around a subject P at high speed like a propeller by a motor installed on a base (not illustrated).

The image processing apparatus 100 comprises, as illustrated in FIG. 1, an analog/digital (A/D) converting circuitry 21, a misregistration determining circuitry 22, a registration circuitry 23, a region of interest (ROI) setting circuitry 24, a profile measuring circuitry 25, a correction-factor determining circuitry 26, a digital subtraction angiography (DSA)-image correcting circuitry 27, a first subtraction circuitry 28, a second subtraction circuitry 29, a filtering circuitry 30, an affine conversion circuitry 31, a look up table (LUT) 32, an image memory 33, a control circuitry 34, and a display 40. Furthermore, although not illustrated, the image processing apparatus 100 comprises an input circuitry such as a mouse and keyboard, a trackball, or a pointing device that receives various operations on the X-ray diagnostic apparatus 1 from an operator.

The display 40 displays thereon various images processed by the image processing apparatus 100 and a variety of information such as a graphical user interface (GUI). For example, the display 40 is a cathode ray tube (CRT) monitor, a liquid crystal display monitor, or the like. The A/D converting circuitry 21 is connected to the FPD 12, and converts an analog signal input from the FPD 12 into a digital signal and stores the converted digital signal as an X-ray acquisition image in the image memory 33. The image memory 33 stores therein an X-ray acquisition image.

The misregistration determining circuitry 22 determines a misregistration between two DSA images taken at different timings. The registration circuitry 23 corrects a misregistration between two DSA images on the basis of a misregistration determined by the misregistration determining circuitry 22. The ROI setting circuitry 24 sets an ROI on a DSA image. Specifically, the ROI setting circuitry 24 extracts a blood vessel having the largest vessel diameter in blood vessels included within a predetermined range of area from the lower end of a DSA image, and calculates a peak value of partial integration value of concentration values with respect to each predetermined region in the extracted blood vessel, and then sets a region of which the calculated peak value is lowest as an ROI.

Figure 2:
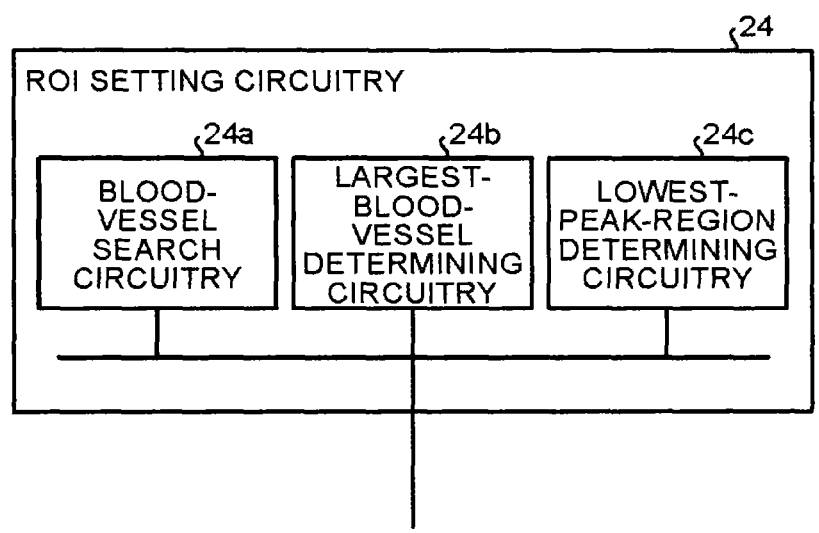
FIG. 2 is an exemplary diagram illustrating an example of a configuration of an ROI setting circuitry according to the first embodiment.

FIG. 2 is an exemplary diagram illustrating an example of a configuration of the ROI setting circuitry 24 according to the first embodiment. As illustrated in FIG. 2, the ROI setting circuitry 24 comprises a blood-vessel search circuitry 24a, a largest-blood-vessel determining circuitry 24b, and a lowest-peak-region determining circuitry 24c. The blood-vessel search circuitry 24a searches on the horizontal axis located outside of a certain range of distance from the lower end of a DSA image for a blood vessel on the basis of the DSA image. The largest-blood-vessel determining circuitry 24b determines a blood vessel having the largest vessel diameter in blood vessels found by the blood-vessel search circuitry 24a. The lowest-peak-region determining circuitry 24c traces the largest blood vessel determined by the largest-blood-vessel determining circuitry 24b in a downward direction, and determines a region of which the peak of partial integration values of concentration values is lowest.

To return to FIG. 1, the profile measuring circuitry 25 measures a profile on an ROI set in a DSA image. Specifically, the profile measuring circuitry 25 measures respective profiles on contrast media concentration in ROIs including blood vessels set at about the same position in two DSA images of subject's head taken from about the same direction at different time phases (shooting times). For example, the profile measuring circuitry 25 measures profiles on contrast media concentration in a region of interest including a major artery which is blood vessels or capillary vessels which are not affected by treatment. The correction-factor determining circuitry 26 determines a correction factor so that two profiles are approximately matched. Specifically, the correction-factor determining circuitry 26 determines a correction factor so that the two profiles measured by the profile measuring circuitry 25 are approximately matched. For example, the correction-factor determining circuitry 26 determines at least one of a gap of the arrival time of a contrast media, a gain relating to subject's cardiac output, and subject's blood flow velocity so that two profiles in two subtraction images are approximately matched.

The DSA-image correcting circuitry 27 corrects at least one of the two DSA images on the basis of the correction factor determined by the correction-factor determining circuitry 26. The first subtraction circuitry 28 performs subtraction of images taken before and after administration of a contrast media. The second subtraction circuitry 29 performs subtraction of the DSA image corrected by the DSA-image correcting circuitry 27 and the other DSA image. The filtering circuitry 30 performs high-frequency emphasis filtering, etc. The affine conversion circuitry 31 performs scaling, movement and rotation of an image, etc. The LUT 32 performs tone conversion.

The control circuitry 34 controls the entire X-ray diagnostic apparatus 1. Specifically, the control circuitry 34 controls various processes involved in acquisition of X-ray acquisition images, generation of a display image, display of a display image on the display 40, etc. For example, the control circuitry 34 controls so as to display information (for example, difference information etc.) based on two DSA images that at least one thereof has been corrected by the DSA-image correcting circuitry 27 on the display 40.

With the above-described configuration, the X-ray diagnostic apparatus 1 according to the first embodiment enables an accurate comparison between a preoperative image and a postoperative image which was difficult for the conventional technology to make.

For example, in the neuro-vascular treatment using an X-ray diagnostic apparatus, there is treatment to insert a catheter to a stenosis segment via blood vessel and widen the stenosis segment by inflating a balloon attached around the catheter. This treatment is called intervention. In the intervention, when the balloon is inflated, a small debris of part of the stenosis segment flows to the peripheral small vessel, and the small debris may cause an infarction in a capillary vessel.

Accordingly, after the intervention, a brain perfusion image acquired with CT apparatus is used to check whether an infarction has occurred or not. Furthermore, in the conventional technology, abnormal blood flow is checked, for example, by comparative reading of blood flow states of the right and left hemispheres. However, in the above-described conventional technology, the preoperative state is not reflected; therefore, an infarction which has already occurred before the treatment, a tendency of some densely staining, etc. may be misdetermined. For example, even in the case of a patient who has chronically been afflicted with an infarction and required no treatment for the infarction, the already-developed infarction may be diagnosed as a newly-developed infarction caused by treatment, and unnecessary thrombolytic therapy may be given.

Figure 3:
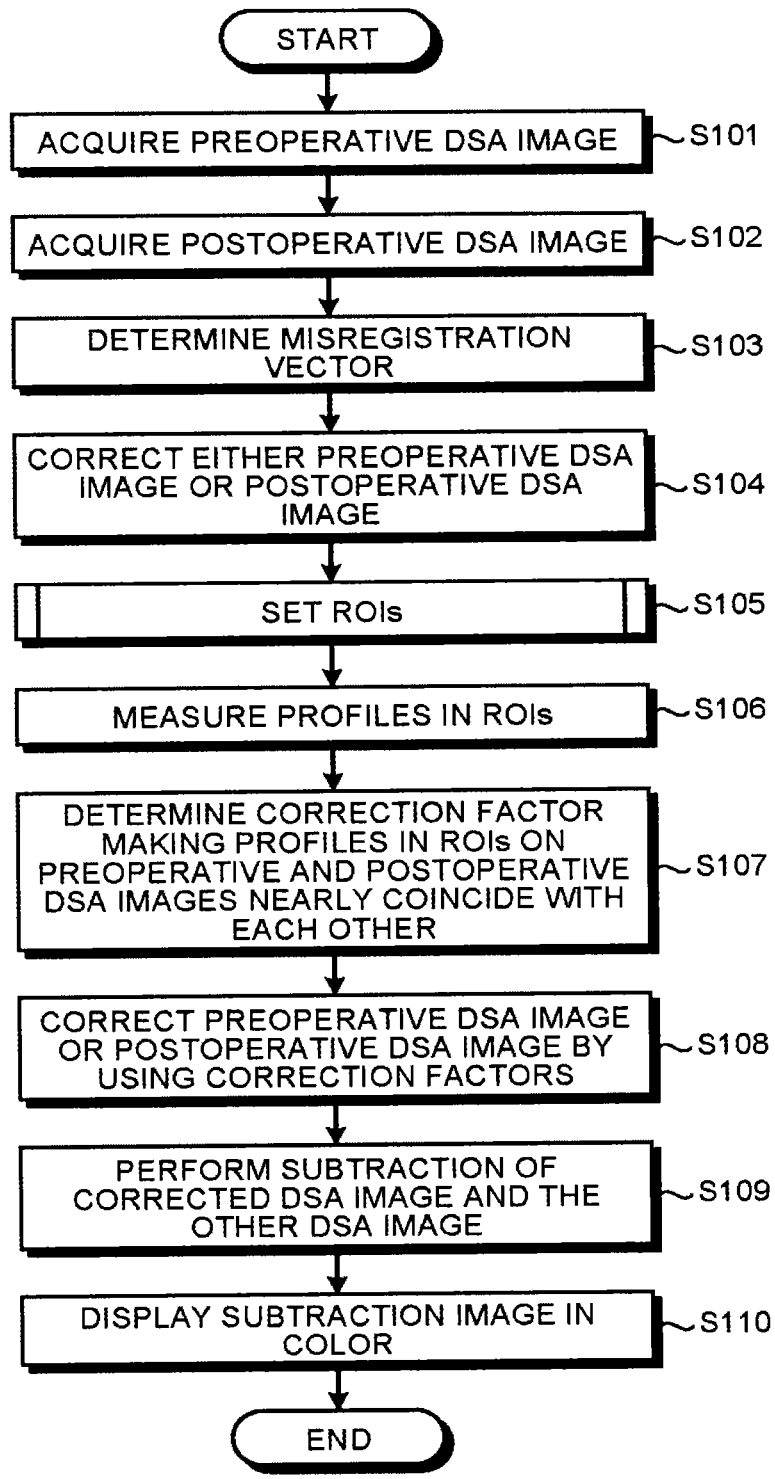
FIG. 3 is an exemplary flowchart illustrating a procedure of a process performed by the X-ray diagnostic apparatus according to the first embodiment.

Consequently, the X-ray diagnostic apparatus 1 according to the present embodiment performs a process to be described in detail below, thereby enabling intervention and an accurate comparison between images before and after a procedure such as thrombolytic therapy. FIG. 3 is an exemplary flowchart illustrating a procedure of the process performed by the X-ray diagnostic apparatus 1 according to the first embodiment.

As illustrated in FIG. 3, the X-ray diagnostic apparatus 1 first acquires a preoperative DSA image before medical treatment such as thrombolytic therapy (S101). Specifically, the X-ray diagnostic apparatus 1 sets the C-shaped arm 13 in an arbitrary direction, and takes a few frames of mask images before contrast injection, and then takes contrast images continuously while a contrast media flows through blood vessels. The few frames of mask images and the multiple contrast images are each converted into a digital signal and stored in the image memory 33 by the A/D converting circuitry 21.

The first subtraction circuitry 28 reads out the few frames of mask images stored in the image memory 33, and generates an average mask image with less noise by averaging the read mask images. Then, the first subtraction circuitry 28 performs subtraction (Log subtraction) of the average mask image from each of the multiple contrast images, thereby generating a preoperative DSA image.

When the preoperative DSA image has been generated by the first subtraction circuitry 28, the control circuitry 34 displays a dynamic image of the generated preoperative DSA image on the display 40. Incidentally, the generated preoperative DSA image is stored in the image memory 33.

After, for example, medical treatment such as thrombolytic therapy are performed, the X-ray diagnostic apparatus 1 acquires a postoperative DSA image by specifying the same data acquisition program for the preoperative DSA image thereby performing the same data acquisition as the preoperative (S102).

Then, the control circuitry 34 displays a dynamic image of the generated postoperative DSA image on the display 40. Incidentally, the generated postoperative DSA image is stored in the image memory 33.

Then, when having received an instruction to compare blood flow between the preoperative DSA image and the postoperative DSA image from a user through a GUI (not illustrated), the misregistration determining circuitry 22 reads out the average mask images of the preoperative and postoperative DSA images from the image memory 33, and determines a misregistration vector (S103). For example, the misregistration determining circuitry 22 determines a misregistration vector between a mask image ($M_{pre}$(i, j)) of the preoperative DSA image and a mask image ($M_{post}$(i, j)) of the postoperative DSA image by the following equation (1). Here, CR($\Delta$i, $\Delta$j) in equation (1) denotes a difference between ($M_{pre}$(i, j)) and ($M_{post}$(i, j)). Furthermore, N in equation (1) denotes image size.

$$CR(\Delta i, \Delta j) = \sum_{i=1}^{N}\sum_{j=1}^{N} \{M_{post}(i, j) - M_{pre}(i + \Delta i, j + \Delta j)\}^2 \quad (1)$$

The misregistration determining circuitry 22 searches for a vector ($\Delta$i, $\Delta$j) whose CR($\Delta$i, $\Delta$j) is minimum while changing elements of the vector ($\Delta$i, $\Delta$j) gradually and separately by the iterative algorithm. Then, the misregistration determining circuitry 22 sends the final vector ($\Delta$i, $\Delta$j) to the registration circuitry 23. Incidentally, here, for the sake of simplicity of explanation, there is described a case where a misregistration in a two-dimensional movement is suspected; however, it is preferable to further detect a misregistration in a rotation direction. That is, it is preferable that the misregistration determining circuitry 22 determines a vector ($\Delta$i, $\Delta$j, $\Delta\theta$).

Then, when the registration circuitry 23 has received misregistration vector from the misregistration determining circuitry 22, the registration circuitry 23 corrects either the preoperative DSA image or the postoperative DSA image by using the received misregistration vector "($\Delta$i, $\Delta$j)" or "($\Delta$i, $\Delta$j, $\Delta\theta$)" (S104).

Figure 4:
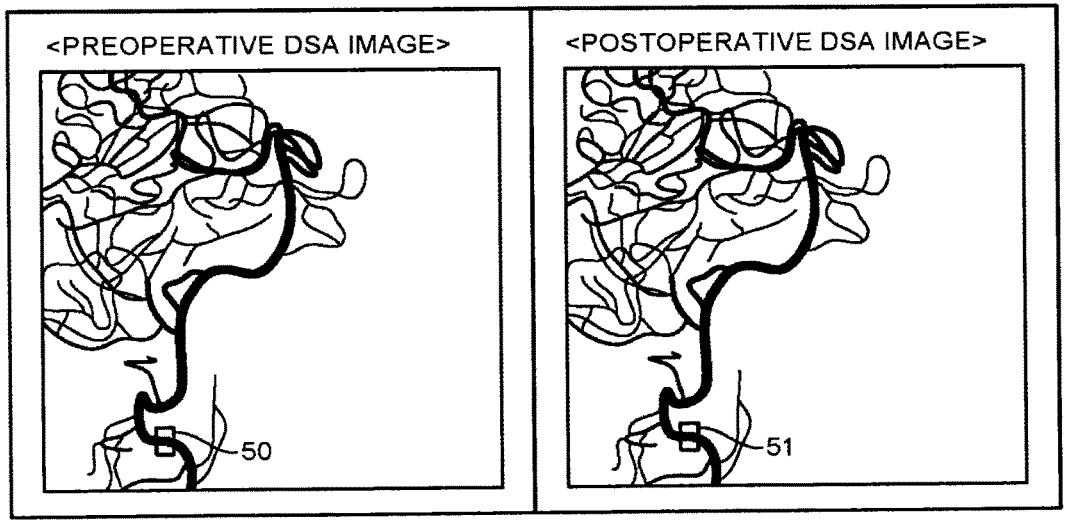
FIG. 4 is an exemplary diagram illustrating an example of an ROI set by the ROI setting circuitry according to the first embodiment.

Then, the ROI setting circuitry 24 sets ROIs in the DSA images, respectively (S105). Specifically, using either one of the preoperative and postoperative DSA images of which the misregistration has been corrected, the ROI setting circuitry 24 sets ROIs at about the same position in the preoperative DSA image and the postoperative DSA image. For example, the ROI setting circuitry 24 calculates the position of a major artery in at least one of the two subtraction images, and sets a region including the calculated major artery as an ROI. FIG. 4 is an exemplary diagram illustrating an example of an ROI set by the ROI setting circuitry 24 according to the first embodiment.

Figure 5:
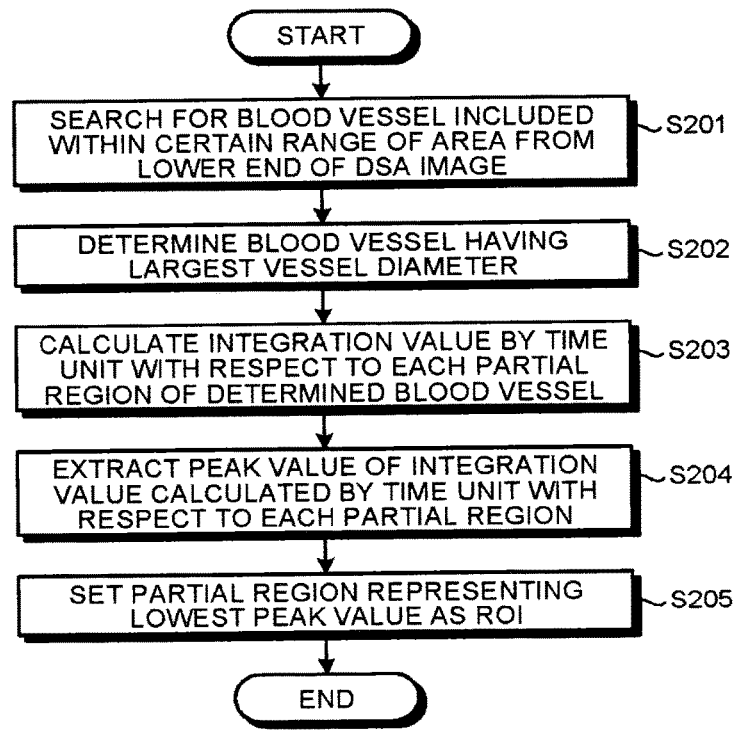
FIG. 5 is an exemplary flowchart illustrating a procedure of a process performed by the ROI setting circuitry according to the first embodiment.

As illustrated in FIG. 4, the ROI setting circuitry 24 sets ROIs 50 and 51 in the preoperative and postoperative DSA images, respectively. Here, the details of a process performed by the ROI setting circuitry 24 are explained below. FIG. 5 is an exemplary flowchart illustrating a procedure of the process performed by the ROI setting circuitry 24 according to the first embodiment. Incidentally, the process illustrated in FIG. 5 corresponds to the process at Step S105 in FIG. 3.

Figure 6A:
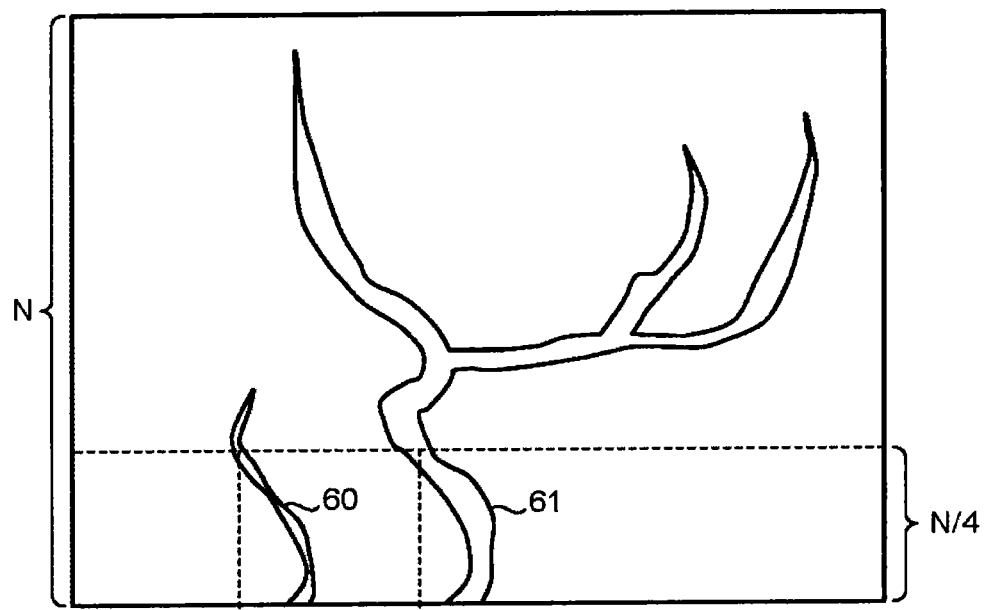
FIGS. 6A and 6B are an exemplary diagram for explaining an example of a process performed by a blood-vessel search circuitry according to the first embodiment.
Figure 6B:
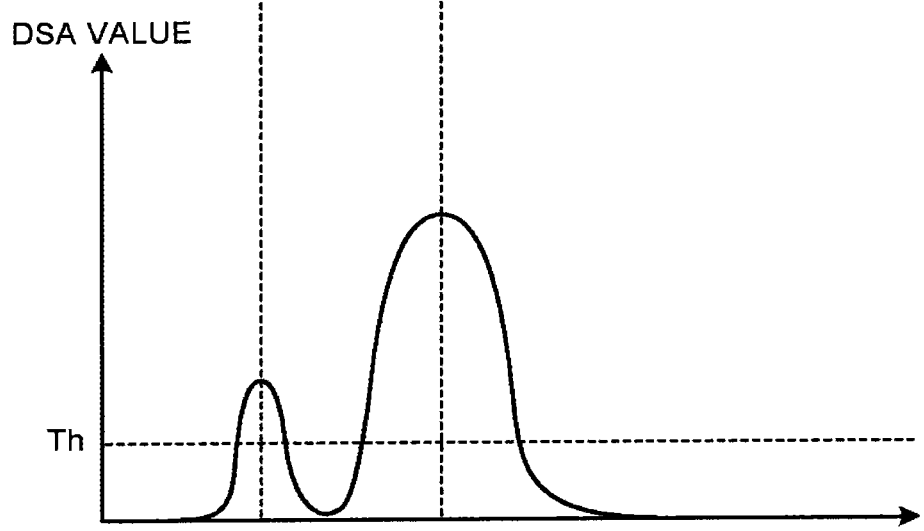

As illustrated in FIG. 5, in the ROI setting circuitry 24, the blood-vessel search circuitry 24a uses either one of the preoperative and postoperative DSA images of which the misregistration has been corrected, and searches for a blood vessel included within a certain range of area from the lower end of the DSA image (S201). FIGS. 6A and 6B are an exemplary diagram for explaining an example of a process performed by the blood-vessel search circuitry 24a according to the first embodiment. FIG. 6A illustrates a case of a search for a blood vessel in a DSA image in an image size of "N×N".

For example, as illustrated in FIG. 6A, the blood-vessel search circuitry 24a sets a position at a distance of quarter of N from the lower end of the DSA image as an initial position of blood vessel search. Then, as illustrated in FIG. 6B, the blood-vessel search circuitry 24a measures a profile of a DSA value on the horizontal axis at the position of quarter of N from the lower end of DSA image. After that, the blood-vessel search circuitry 24a extracts a peak of which the DSA value exceeds a predetermined threshold "Th" in the measured profile as a blood vessel. For example, as illustrated in FIGS. 6A and 6B, the blood-vessel search circuitry 24a extracts blood vessels 60 and 61 corresponding to peaks that exceed "Th". Then, the blood-vessel search circuitry 24a transmits the profile and position information of the blood vessels 60 and 61 to the largest-blood-vessel determining circuitry 24b.

The largest-blood-vessel determining circuitry 24b determines a blood vessel having the largest vessel diameter in blood vessels extracted by the blood-vessel search circuitry 24a (S202). For example, the largest-blood-vessel determining circuitry 24b measures a vessel diameter (width of a peak) from a result of the profile illustrated in FIG. 6B, and determines the blood vessel 61 having the largest vessel diameter as the largest blood vessel. Then, the largest-blood-vessel determining circuitry 24b transmits information on the measured vessel diameters and position information of the blood vessel 61 to the lowest-peak-region determining circuitry 24c. As described above, the blood-vessel search circuitry 24a searches for a blood vessel with the position of quarter of N from the lower end of a DSA image as an initial position of blood vessel search, and the largest-blood-vessel determining circuitry 24b determines a blood vessel having the largest vessel diameter, thereby a major artery can be extracted as a blood vessel on which an ROI is set.

Figure 7A:
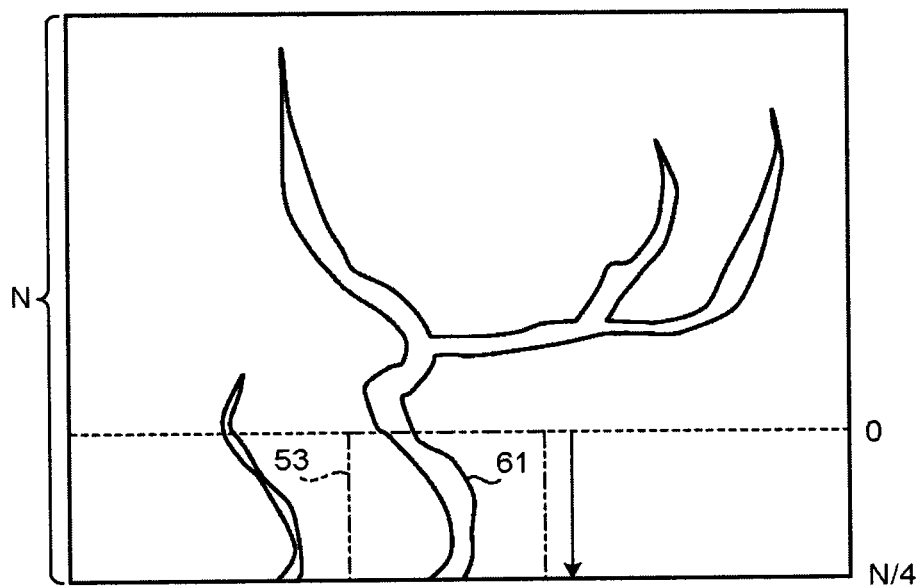
FIG. 7A is an exemplary diagram for explaining a process for a lowest-peak-region determining circuitry according to the first embodiment to calculate an integration value with respect to each partial region.
Figure 7B:
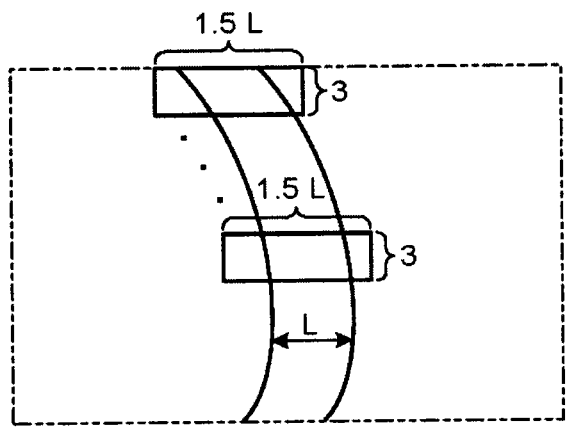
FIG. 7B is an exemplary diagram for explaining the process for the lowest-peak-region determining circuitry according to the first embodiment to calculate an integration value with respect to each partial region.
Figure 7C:
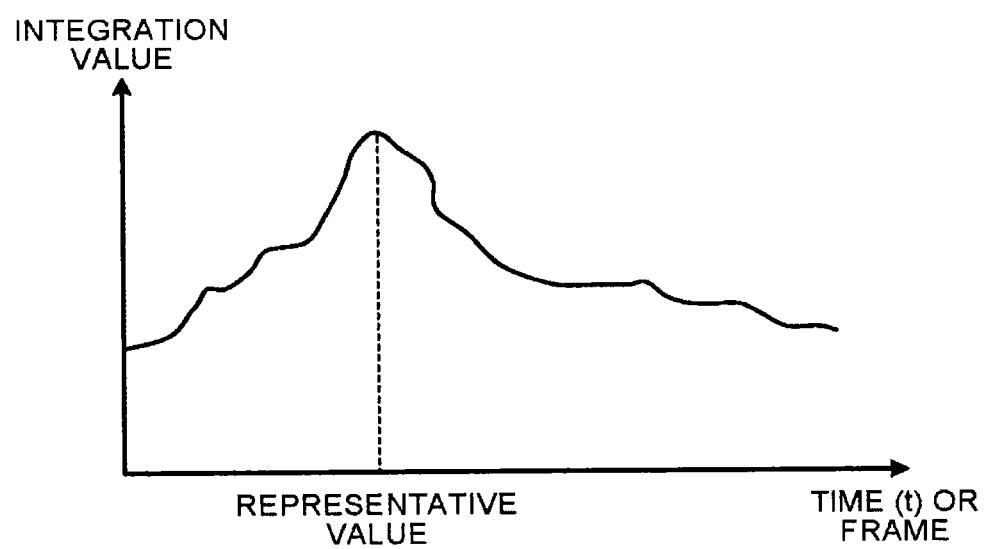
FIG. 7C is an exemplary diagram for explaining the process for the lowest-peak-region determining circuitry according to the first embodiment to calculate an integration value with respect to each partial region.

The lowest-peak-region determining circuitry 24c calculates an integration value of concentration values by time unit with respect to each partial region of the blood vessel determined by the largest-blood-vessel determining circuitry 24b (S203). Specifically, the lowest-peak-region determining circuitry 24c calculates an integration value of concentration values of each partial region by time unit while tracing the center of the blood vessel downward from the position of quarter of N on the vertical direction in the DSA image. FIGS. 7A to 7C are exemplary diagrams for explaining a process for the lowest-peak-region determining circuitry 24c according to the first embodiment to calculate an integration value of each partial region. Incidentally, FIG. 7B is an enlarged view of a region 53 in FIG. 7A.

For example, as illustrated in FIG. 7A, the lowest-peak-region determining circuitry 24c calculates an integration value of concentration values of each partial region while tracing the vessel center of the blood vessel 61 downward from the position of quarter of N from the lower end of the DSA image on the vertical direction. Here, for example, as illustrated in FIG. 7B, the lowest-peak-region determining circuitry 24c sets a rectangle of "1.5 L (=1.5×a vessel diameter)" in width and "3 pixels" in height as a partial region, and calculates an integration value with respect to each partial region. Incidentally, the size of a partial region can be arbitrarily set by a user.

The lowest-peak-region determining circuitry 24c calculates an integration value of concentration values with respect to each partial region of each of DSA images while a contrast media is flowing. That is, the lowest-peak-region determining circuitry 24c calculates a temporal change in an integration value as illustrated in FIG. 7C with respect to each partial region.

Then, the lowest-peak-region determining circuitry 24c extracts a peak value of integration value calculated by time unit with respect to each partial region (S204). For example, as illustrated in FIG. 7C, the lowest-peak-region determining circuitry 24c extracts a representative value of which the integration value is at peak with respect to each partial region.

Figure 8:
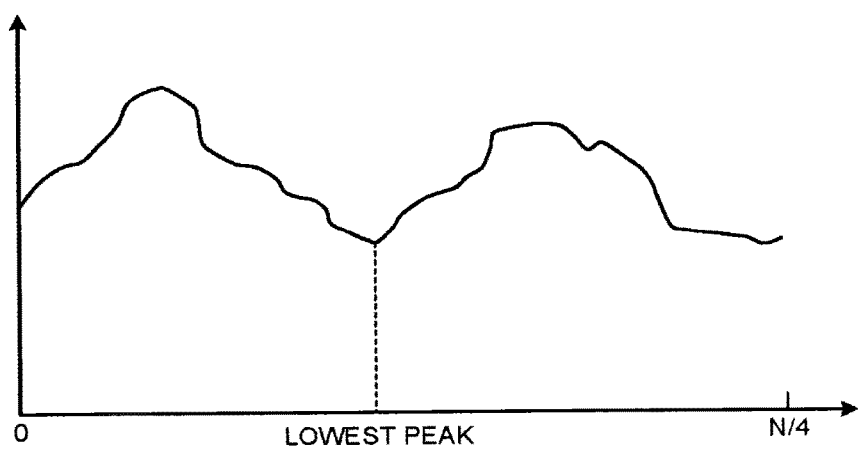
FIG. 8 is an exemplary diagram for explaining a process for the lowest-peak-region determining circuitry according to the first embodiment to extract the lowest peak.

After that, the lowest-peak-region determining circuitry 24c sets a partial region representing the lowest peak value as an ROI (S205). Specifically, the lowest-peak-region determining circuitry 24c compares the representative values of partial regions, and sets a partial region representing the minimum value as an ROI. FIG. 8 is an exemplary diagram for explaining a process for the lowest-peak-region determining circuitry 24c according to the first embodiment to extract the lowest peak. In FIG. 8, the horizontal axis represents "0" to "N/4" illustrated in FIG. 7A, and the vertical axis represents an integration value. That is, FIG. 8 illustrates a graph in which a representative value of each partial region is plotted.

For example, as illustrated in FIG. 8, the lowest-peak-region determining circuitry 24c plots a representative value of each partial region on the graph, and determines the lowest peak. Then, the lowest-peak-region determining circuitry 24c sets a partial region corresponding to the determined lowest peak as an ROI.

As described above, the lowest-peak-region determining circuitry 24c sets a partial region representing the minimum value in the representative values of partial regions as an ROI. That is, the lowest-peak-region determining circuitry 24c sets a partial region with the least temporal change in an integration value as an ROI. A major artery on which an ROI is set changes little in vessel diameter; however, a concentration value of an actual major artery changes significantly. This is mainly due to the course of a blood vessel and beam hardening.

For example, when the course of a blood vessel is at an angle of 90 degrees to an X-ray irradiation direction, an amount of contrast media exposed to X-rays is equivalent to only the thickness of a diameter of the blood vessel, and a concentration value is minimum. However, when the course of a blood vessel is parallel to the X-ray irradiation direction, an amount of contrast media exposed to X-rays is equivalent to the depth of the running blood vessel, and a concentration value is maximum.

Therefore, when the course of a blood vessel is parallel to the X-ray irradiation, it is not possible to correctly assess the blood flow, so it is preferable to set a region in which the course of the blood vessel is at an angle of about 90 degrees to the X-ray irradiation direction as an ROI. Accordingly, the lowest-peak-region determining circuitry 24c sets a partial region of which the integration value of concentration values is minimum as an ROI, thereby extracting a region in which the course of the blood vessel is at an angle of about 90 degrees to the X-ray irradiation.

Furthermore, for example, in a blood vessel region overlapping a thick bone, a concentration value decreases due to beam hardening. Accordingly, the ROI setting circuitry 24 can be configured to calculate an X-ray transmittance with respect to each partial region on the basis of a concentration value of a mask image used in generation of a DSA image and set a region of which the calculated X-ray transmittance is low not to be a subject for an ROI.

The process performed by the ROI setting circuitry 24 is explained above. To return to FIG. 3, as described above, when the ROIs have been set in the DSA images, information on the ROIs is sent to the profile measuring circuitry 25. The profile measuring circuitry 25 measures profiles in the ROIs set by the ROI setting circuitry 24 (S106).

Figure 9:
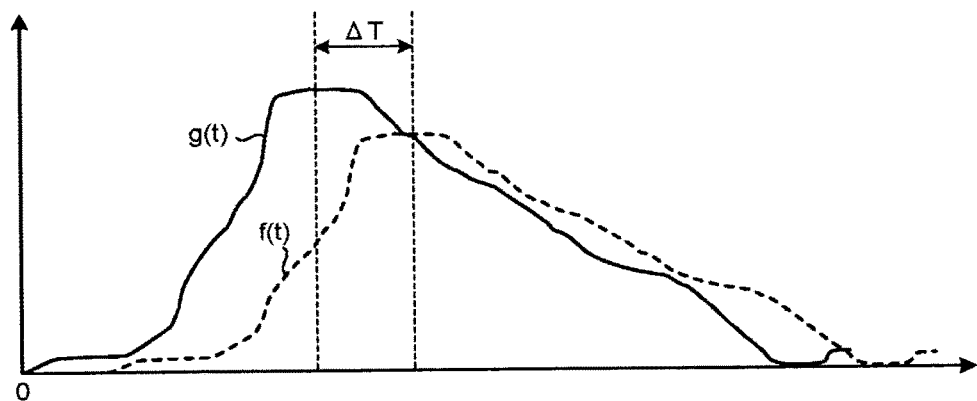
FIG. 9 is an exemplary diagram for explaining an example of a process performed by a profile measuring circuitry according to the first embodiment.

Specifically, the profile measuring circuitry 25 reads out the DSA image of which the misregistration has been corrected and the other DSA image from the image memory 33, and measures a profile on the average value or sum of DSA pixel values in an ROI with respect to each of the read DSA images. FIG. 9 is an exemplary diagram for explaining an example of a process performed by the profile measuring circuitry 25 according to the first embodiment.

For example, as illustrated in FIG. 9, the profile measuring circuitry 25 measures a profile "f(t)" of the preoperative DSA image and a profile "g(t)" of the postoperative DSA image. Here, "ΔT" illustrated in FIG. 9 denotes a delay time to arrival of a contrast media at an ROI. Information on the profiles measured by the profile measuring circuitry 25 is sent to the correction-factor determining circuitry 26.

When the correction-factor determining circuitry 26 has acquired the information on the profiles in the ROIs, the correction-factor determining circuitry 26 determines a correction factor making the profiles in the ROIs on the preoperative and postoperative DSA images nearly coincide with each other (S107). For example, the correction-factor determining circuitry 26 determines a correction factor making the profile "f(t)" of the preoperative DSA image and the profile "g(t)" of the postoperative DSA image nearly coincide with each other by the following equation (2).

$$E=\|f(t)-\alpha g\{T(t-\Delta t)\}\|^2 \quad (2)$$

The correction-factor determining circuitry 26 searches for "α", "Δt", and "T" keeping "E" at a minimum while changing a gain "α", a delay time "Δt" to arrival of a contrast media, and a blood flow velocity "T". That is, using the gain "α" for correcting a difference in patient's cardiac output between before and after medical treatment, "Δt" for correcting a delay time to arrival of a contrast media caused by a misregistration of the catheter at the time of administration of the contrast media between before and after medical treatment, and the blood flow velocity "T" for correcting a difference in patient's heart rate between before and after medical treatment, the correction-factor determining circuitry 26 makes the two profiles nearly coincide with each other. Then, the correction-factor determining circuitry 26 sends the found "α", "Δt", and "T" to the DSA-image correcting circuitry 27.

Incidentally, there is described above an example where all of correction factors "α", "Δt", and "T" are found. However, the embodiment is not limited to this; for example, when it can be assumed that patient's heartbeat is stable and the blood flow velocity is virtually constant, "T" can be a fixed velocity of "T=1". By doing so, determination of a correction factor can be performed at high speed.

The DSA-image correcting circuitry 27 corrects the preoperative DSA image or the postoperative DSA image by using the correction factors "α", "Δt", and "T" received from the correction-factor determining circuitry 26 (S108). Here, correction of a DSA image is generally correction of a preoperative DSA image; however, in the present embodiment, either DSA image can be corrected. The DSA image corrected by the DSA-image correcting circuitry 27 is stored in the image memory 33.

Incidentally, here, the correction factors are determined by using DSA images for checking the blood flow states before and after medical treatment. However, a correction factor can be determined by using DSA images that were taken at about the same time and are not affected by medical treatment, etc. Specifically, for example, when endovascular treatment of the right internal carotid artery is performed, preoperative and postoperative DSA images of the left internal carotid artery are taken at times before and after the timing to take preoperative and postoperative DSA images of the right internal carotid artery. As these images are thought to be not affected by the treatment, etc., there is an advantage that a correction factor can be determined stably.

When the DSA image has been corrected by the DSA-image correcting circuitry 27, the second subtraction circuitry 29 reads out the corrected DSA image and the other DSA image from the image memory 33, and performs subtraction (S109). For example, the second subtraction circuitry 29 performs subtraction of the corrected DSA image and the other DSA image by the following equation (3).

$$C(i,j)=\alpha g_{(i,j)}\{T(t-\Delta t)\}-f_{(i,j)}(t) \quad (3)$$

Here, C(i, j) in equation (3) denotes a blood-flow check image. Furthermore, in equation (3), $f_{(i,j)}(t)$ denotes the preoperative DSA image, and $g_{(i,j)}(t)$ denotes the postoperative DSA image. Moreover, equation (3) represents an equation when the postoperative DSA image is corrected. As illustrated in equation (3), the second subtraction circuitry 29 subtracts the preoperative DSA image from the corrected postoperative DSA image, thereby generating a blood-flow check image. The blood-flow check image (a subtraction image) generated by the second subtraction circuitry 29 is stored in the image memory 33.

Figure 10:
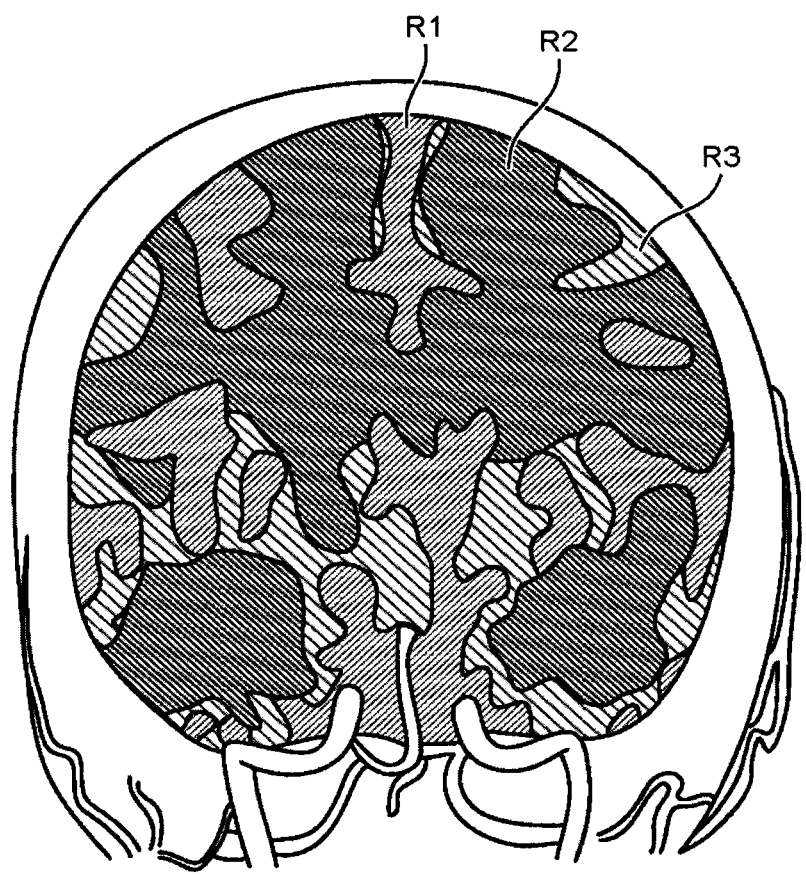
FIG. 10 is an exemplary diagram illustrating an example of a blood-flow check image displayed on a display according to the first embodiment.

Then, the blood-flow check image generated by the second subtraction circuitry 29 is stored in the image memory 33 and sent to the control circuitry 34, and is displayed in color on the display 40 by the control circuitry 34 (S110). For example, the display 40 displays thereon a perfusion image based on a result of the subtraction of the two DSA images that at least one thereof has been corrected. FIG. 10 is an exemplary diagram illustrating an example of the blood-flow check image displayed on the display 40 according to the first embodiment.

For example, as illustrated in FIG. 10, the control circuitry 34 converts pixel values into colors (for example, converts a region in which the blood flow is increased sufficiently (such as a region R1 in FIG. 10) into red, a region in which the blood flow is decreased sufficiently (such as a region R2 in FIG. 10) into blue, and an intermediate region (such as a region R3 in FIG. 10) into yellow), and displays the converted image on the display 40. Incidentally, the displayed blood-flow check image can be a black-and-white image.

As described above, the X-ray diagnostic apparatus 1 according to the first embodiment continuously displays blood-flow check images obtained by subtraction of two preoperative and postoperative DSA images that at least one thereof has been corrected according to a time series, thereby displaying a color or black-and-white dynamic image. Here, besides the above-described dynamic image, the X-ray diagnostic apparatus 1 according to the first embodiment can display various analysis results. For example, the X-ray diagnostic apparatus 1 can display a graph representing a change in the blood flow state between before and after medical treatment with respect to each predetermined region of the DSA images.

FIGS. 11A to 11F are exemplary diagrams each illustrating an example of an analysis result displayed on the display according to the first embodiment. FIGS. 11A, 11C and 11E illustrate preoperative and postoperative profiles in a predetermined region, and FIGS. 11B, 11D and 11F illustrate difference information on a difference between the preoperative and postoperative profiles. Incidentally, FIGS. 11A to 11C illustrate difference information when the preoperative profile "f(t)" is subtracted from the corrected postoperative profile "g(t)".

For example, with respect to predetermined regions of the two preoperative and postoperative DSA images that at least one thereof has been corrected by the correction factors determined by a region including a major artery or a region including capillary vessels which are not affected by treatment, the control circuitry 34 displays profiles of the preoperative and postoperative DSA images and difference information on the display 40. For example, as illustrated in (A) of FIG. 11A, the control circuitry 34 displays a profile "f(t)" of a predetermined region in the preoperative DSA image and a profile "g(t)" of the same region in the postoperative DSA image on the display 40. Furthermore, as illustrated in (B) of FIG. 11A, the control circuitry 34 displays a graph 71 obtained by subtracting the preoperative profile "f(t)" from the corrected postoperative profile "g(t)" on the display 40. Graphs 72 and 73 illustrated in (B) of FIGS. 11B and 11C, respectively, are also obtained by subtracting the preoperative profile "f(t)" from the corrected postoperative profile "g(t)" of the profiles shown in (A) of FIGS. 11B and 11C.

Here, the predetermined region of which the profiles and graph are displayed illustrated in the diagram can be arbitrarily specified by an operator. Furthermore, the entire image can be exhaustively displayed in a predetermined size of area. This enables the operator to make a detailed observation of how the region of which the profiles and graph are displayed changes before and after medical treatment. For example, when the profiles and graphs illustrated in FIGS. 11A and 11B are displayed, the operator can determine that the blood flow state in the corresponding region has been improved after medical treatment.

Likewise, from the profiles and graphs illustrated in FIGS. 11C to 11F, the operator can easily determine how a corresponding region changes before and after medical treatment. For example, when the profiles and graphs illustrated in FIGS. 11C and 11D are displayed on the display 40, the operator can determine that there is a slight delay in the blood flow after medical treatment, and can suspect that a slight stenosis may have occurred. Furthermore, for example, when the profiles and graphs illustrated in FIGS. 11E and 11F are displayed on the display 40, the operator can determine that the blood flow is worse after medical treatment, and can suspect that a minor infarction may have occurred.

Incidentally, in FIGS. 11A to 11F, there is described the graph obtained by subtracting the preoperative profile "f(t)" from the corrected postoperative profile "g(t)"; however, the embodiment is not limited to this. That is, it can be a graph obtained by subtracting the corrected postoperative profile "g(t)" from the preoperative profile "f(t)".

Figure 12:
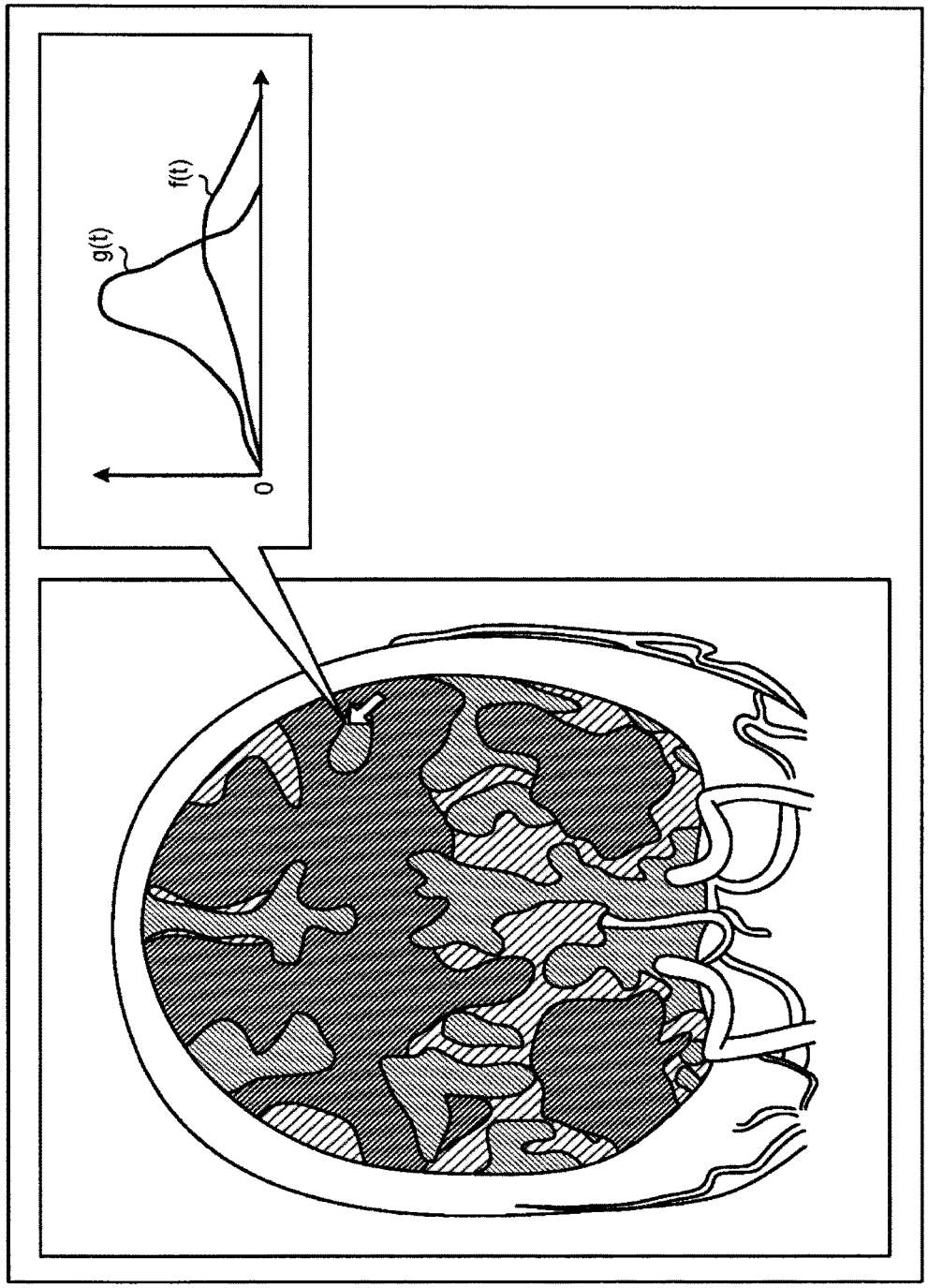
FIG. 12 is an exemplary diagram illustrating an example of display information displayed on the display according to the first embodiment.

Furthermore, the X-ray diagnostic apparatus 1 according to the first embodiment can display a blood-flow check image and profiles corresponding to a region of the blood-flow check image, etc. FIG. 12 is an exemplary diagram illustrating an example of display information displayed on the display according to the first embodiment. As illustrated in FIG. 12, when the operator has specified a point or region on the blood-flow check image through the input circuitry, the control circuitry 34 displays preoperative and postoperative profiles of the specified point or region. Incidentally, FIG. 12 illustrates only the profiles; however, a difference graph can also be displayed.

In this manner, the X-ray diagnostic apparatus 1 according to the first embodiment can display profiles, a difference graph, etc. of each predetermined region in addition to a blood-flow check image. Furthermore, the X-ray diagnostic apparatus 1 according to the first embodiment can also display a blood-flow-volume difference indicating a difference in volume flow of blood in a predetermined region and a difference degree indicating a difference between preoperative blood flow and postoperative blood flow. The blood-flow-volume difference and the difference degree are explained below with the following equations (4) to (7). Incidentally, in equations (4) to (7), there is explained an example where out of the above-described correction factors "α", "Δt", and "T", "α" and "Δt" are used to correct a DSA image.

That is, the correction-factor determining circuitry 26 determines "α" and "Δt" so that the profile "f(t)" in the ROI of the preoperative DSA image and the profile "g(t)" in the ROI of the postoperative DSA image, which have been measured by the profile measuring circuitry 25, satisfy equation (4). Incidentally, "α" is a gain for correcting a difference in patient's cardiac output between before and after medical treatment, and "Δt" is for correcting a delay time to arrival of a contrast media caused by a misregistration of the catheter at the time of administration of the contrast media between before and after medical treatment.

$$f(t) \approx \alpha g(t - \Delta t) \quad (4)$$

Then, the second subtraction circuitry 29 performs subtraction of the corrected DSA image and the other DSA image by the following equation (5). Here, COMP(t) in equation (5) denotes a difference between the DSA images. Furthermore, in equation (5), $f_{(i,j)}(t)$ denotes the preoperative DSA image, and $g_{(i,j)}(t)$ denotes the postoperative DSA image. Moreover, equation (5) represents an equation when the postoperative DSA image is corrected.

$$COMP(t) = \alpha g_{(i,j)}(t - \Delta t) - f_{(i,j)}(t) \quad (5)$$

As illustrated in equation (5), the second subtraction circuitry 29 subtracts the preoperative DSA image from the corrected postoperative DSA image with respect to each pixel. Then, the control circuitry 34 calculates a blood-flow-volume difference by the following equation (6) using COMP(t) calculated by the second subtraction circuitry 29. That is, the control circuitry 34 calculates a blood-flow-volume difference and difference degree on the basis of region-by-region profiles calculated based on the corrected subtraction image. Here, N in equation (6) denotes image size. Furthermore, in equation (6), COMP(n) denotes a difference with respect to each pixel.

$$DifV = \frac{1}{N} \sum_{n=1}^{N} COMP(n) \quad (6)$$

As illustrated in equation (6), the control circuitry 34 calculates an average of the pixel-by-pixel differences as a difference in volume flow of blood, and displays the calculated average on the display 40. Furthermore, the control circuitry 34 calculates a difference degree by the following equation (7) using COMP(t) calculated by the second subtraction circuitry 29. Here, DifE in equation (7) denotes a difference degree. Furthermore, in equation (7), N denotes image size. Moreover, in equation (7), COMP(n) denotes a difference with respect to each pixel.

$$DifE = \frac{1}{N} \sum_{n=1}^{N} COMP(n)^2 \quad (7)$$

As illustrated in equation (7), the control circuitry 34 calculates an average of the square of the pixel-by-pixel differences as a difference degree, and displays the calculated average on the display 40. In this way, the X-ray diagnostic apparatus 1 according to the first embodiment can calculate and display a blood-flow-volume difference and a difference degree in addition to a blood-flow check image, profiles, and a difference graph. Incidentally, the blood-flow-volume difference and the difference degree can be used properly by the operator according to the situation.

Here, the above-described equations for the blood-flow-volume difference and the difference degree are just examples, and the blood-flow-volume difference and the difference degree can be calculated by other equations. For example, the blood-flow-volume difference and the difference degree can be standardized by the preoperative and postoperative profiles. A case where the blood-flow-volume difference and the difference degree are standardized by the preoperative and postoperative profiles is explained below with equations (8) to (13). Incidentally, in equations (8) to (13), only the right sides of the equations for a blood-flow-volume difference DifV and a difference degree DifE are depicted.

For example, the control circuitry 34 calculates a blood-flow-volume difference standardized by a preoperative profile by the following equation (8), and calculates a difference degree standardized by the preoperative profile by the following equation (9). Here, in equations (8) and (9), "f(n)" denotes the preoperative profile. Here, "β" in equations (8) and (9) is for preventing the denominator from being zero, and a sufficiently-smaller value than a value of a blood vessel region of "f(n)" is set as "β".

$$\frac{1}{N}\sum_{n=1}^{N}\frac{COMP(n)}{f(n)+\beta} \tag{8}$$

$$\frac{1}{N}\sum_{n=1}^{N}\left\{\frac{COMP(n)}{f(n)+\beta}\right\}^2 \tag{9}$$

Furthermore, for example, the control circuitry 34 calculates a blood-flow-volume difference standardized by a postoperative profile by the following equation (10), and calculates a difference degree standardized by the postoperative profile by the following equation (11). Here, in equations (10) and (11), "g(n)" denotes the postoperative profile, and there is described a case where the postoperative image is corrected by the correction factors. Here, "β" in equations (10) and (11) is for preventing the denominator from being zero, and a sufficiently-smaller value than a value of a blood vessel region of "f(n)" is set as "β".

$$\frac{1}{N}\sum_{n=1}^{N}\frac{COMP(n)}{\alpha g(n-\Delta t)+\beta} \tag{10}$$

$$\frac{1}{N}\sum_{n=1}^{N}\left\{\frac{COMP(n)}{\alpha g(n-\Delta t)+\beta}\right\}^2 \tag{11}$$

Moreover, for example, the control circuitry 34 calculates a blood-flow-volume difference standardized by an average of the preoperative and postoperative profiles by the following equation (12), and calculates a difference degree standardized by an average of the preoperative and postoperative profiles by the following equation (13). Here, in equations (12) and (13), "f(n)" denotes the preoperative profile, "g(n)" denotes the postoperative profile, and there is described a case where the postoperative image is corrected by the correction factors. Here, "β" in equations (12) and (13) is for preventing the denominator from being zero, and a sufficiently-smaller value than a value of a blood vessel region of "f(n)" is set as "β".

$$\frac{1}{N}\sum_{n=1}^{N}\frac{COMP(n)}{\frac{f(n)+\alpha g(n-\Delta t)}{2}+\beta} \tag{12}$$

$$\frac{1}{N}\sum_{n=1}^{N}\left\{\frac{COMP(n)}{\frac{f(n)+\alpha g(n-\Delta t)}{2}+\beta}\right\}^2 \tag{13}$$

In the above-described examples, there is described the case where the DSA image is corrected by the correction factors "α" and "Δt" as an example; however, the embodiment is not limited to this. That is, the blood-flow-volume difference and the difference degree can be calculated by using the correction factors "α", "Δt", and "T". In this case, the correction-factor determining circuitry 26 determines "α", "Δt", and "T" so that the profile "f(t)" in the ROI of the preoperative DSA image and the profile "g(t)" in the ROI of the postoperative DSA image, which have been measured by the profile measuring circuitry 25, satisfy the following equation (14). Incidentally, "α" is a gain for correcting a difference in patient's cardiac output between before and after medical treatment, and "Δt" is for correcting a delay time to arrival of a contrast media caused by a misregistration of the catheter at the time of administration of the contrast media between before and after medical treatment. Furthermore, "T" denotes a blood flow velocity for correcting a difference in patient's heart rate between before and after medical treatment.

$$f(t) \approx \alpha g\left(\frac{t-\Delta t}{T}\right) \tag{14}$$

As illustrated in equation (14), the X-ray diagnostic apparatus 1 according to the first embodiment can correct the blood flow velocity for correcting a difference in patient's heart rate between before and after medical treatment and calculate a blood-flow-volume difference and difference degree between before and after medical treatment. Accordingly, even if the heart rate varies greatly between before and after medical treatment, it is possible to correct and then analyze these.

As described above, according to the first embodiment, the profile measuring circuitry 25 measures respective profiles on contrast media concentration in ROIs, including blood vessels set at about the same position in two DSA images of subject's head taken from about the same direction at different time phases (acquisition times). Then, the correction-factor determining circuitry 26 determines a correction factor so that the two profiles measured by the profile measuring circuitry 25 are approximately matched. The DSA-image correcting circuitry 27 corrects at least one of the two DSA images on the basis of the correction factor determined by the correction-factor determining circuitry 26. Then, the control circuitry 34 controls so as to display information based on the two DSA images that at least one thereof has been corrected by the DSA-image correcting circuitry 27 on the display 40. Therefore, the X-ray diagnostic apparatus 1 according to the first embodiment can generate and display a subtraction image after the effects of staining of contrast media on the preoperative and postoperative DSA images are approximately matched, and enables an accurate comparison between the preoperative image and the postoperative image.

Furthermore, according to the first embodiment, the first subtraction circuitry 28 calculates a DSA image by subtracting an image little affected by a contrast media from multiple images affected by the contrast media on the basis of two X-ray dynamic images taken at different time phases (acquisition times) while the contrast media is injecting into subject's head from about the same direction. The misregistration determining circuitry 22 determines a misregistration on the basis of the image little affected by the contrast media in the two X-ray dynamic images. The registration circuitry 23 corrects a misregistration of at least one of the two DSA images on the basis of information on the determined misregistration. The profile measuring circuitry 25 measures respective profiles of ROI set at about the same position in the two DSA images including blood vessels that at least one thereof has been corrected. The correction-factor determining circuitry 26 determines a correction factor so that the two profiles measured by the profile measuring circuitry 25 are approximately matched. The DSA-image correcting circuitry 27 corrects at least one of the two DSA images on the basis of the correction factor determined by the correction-factor determining circuitry 26. The control circuitry 34 controls so as to display information based on the two DSA images that at least one thereof has been corrected by the DSA-image correcting circuitry 27 on the display 40. Therefore, the X-ray diagnostic apparatus 1 according to the first embodiment can generate and display a subtraction image after the effects of staining of contrast media on the preoperative and postoperative DSA images are approximately matched, and enables an accurate comparison between the preoperative image and the postoperative image.

Moreover, according to the first embodiment, the ROI is a region including a major artery which are blood vessels or capillary vessels which are not affected by medical treatment. Therefore, the X-ray diagnostic apparatus 1 according to the first embodiment can determine a correction factor by using various regions in an image.

Furthermore, according to the first embodiment, the ROI setting circuitry 24 calculates the position of a major artery in at least one of the two DSA images, and sets a region including the calculated major artery as an ROI. Therefore, the X-ray diagnostic apparatus 1 according to the first embodiment can use the region including the major artery that is not affected by medical treatment and a change in contrast media concentration is evident therein, and enables more accurate determination of a correction factor.

Moreover, according to the first embodiment, the display 40 displays thereon a perfusion image based on a result of the subtraction of the two DSA images that at least one thereof has been corrected. Therefore, the X-ray diagnostic apparatus 1 according to the first embodiment can display a more accurate analysis result.

Furthermore, according to the first embodiment, the correction-factor determining circuitry 26 determines at least one of a time lag to arrival of a contrast media, a gain, and a blood flow velocity so that the two profiles in the two DSA images are approximately matched. Therefore, the X-ray diagnostic apparatus 1 according to the first embodiment can correct the DSA image by using a correction factor that varies the effect of the contrast media greatly, and enables a more accurate comparison between the preoperative DSA image and the postoperative DSA image.

Moreover, according to the first embodiment, the ROI setting circuitry 24 extracts a blood vessel having the largest vessel diameter in blood vessels included within a predetermined range of area from the lower end of a DSA image, and calculates a peak value of integration value of concentration values with respect to each partial region in the extracted blood vessel, and then sets a partial region of which the calculated peak value is lowest as an ROI. Therefore, the X-ray diagnostic apparatus 1 according to the first embodiment can set a region in which the effect of a contrast media on a major artery is high as an ROI, and enables accurate comparative reading.

Furthermore, according to the first embodiment, the ROI setting circuitry 24 calculates an X-ray transmittance with respect to each partial region on the basis of a concentration value of a mask image used in generation of a DSA image, and sets a partial region of which the calculated X-ray transmittance is low not to be a subject for an ROI. Therefore, the X-ray diagnostic apparatus 1 according to the first embodiment can speed up the step of setting an ROI.

Moreover, according to the first embodiment, a blood-flow check image (a subtraction image) is created as a dynamic image; however, the maximum error can be determined pixel by pixel in the dynamic image, and a maximum error image can be displayed as a still image.

Second Embodiment

Although the first embodiment is described heretofore, besides the above-described first embodiment, various other forms may be embodied.

Variation

In the above-described first embodiment, there is described the case where the same data acquisition program as acquisition of a preoperative DSA image is used to acquire a postoperative DSA image. However, the embodiment is not limited to this; for example, a factor that varies the effect of staining of contrast media can be arbitrarily selected, and the selected factor can be configured to be matched before and after medical treatment.

In this case, for example, the control circuitry 34 controls so as to take the postoperative DSA image by matching at least one of an X-ray acquisition condition, an acquisition angle, a field of view (FOV), a source image distance (SID), the position of a collimator, the position of a compensating filter, the size of an X-ray focal spot, a beam-hardening filter, time to injection of contrast media, and an imaging condition with that at the time of acquiring the preoperative DSA image.

In the above-described first embodiment, there is described the case where the ROI setting circuitry 24 automatically sets an ROI in a DSA image. However, the embodiment is not limited to this; for example, an ROI can be set by a user.

In this case, for example, the ROI setting circuitry 24 requests the user to set an ROI. As an example, the ROI setting circuitry 24 displays a message promoting the user to set an ROI on the display 40. The user sets an ROI through a GUI (not illustrated). At this time, the ROI setting circuitry 24 causes the user to set an ROI such that is close to the catheter through which a contrast media is injected and away from an affected part and further such that a blood vessel is parallel to the surface of the detector.

In the above-described first embodiment, there is described the case where the X-ray diagnostic apparatus 1 generates a blood-flow check image; however, the above-described process can be performed by an image processing apparatus such as a workstation. In this case, for example, a workstation connected to an X-ray diagnostic apparatus or image storage device via a network acquires image data from the X-ray diagnostic apparatus or image storage device. Then, the workstation performs the above-described process by using the acquired image data.

As explained above, according to the first and second embodiments, the X-ray diagnostic apparatus and image processing apparatus according to the present embodiments enables an accurate comparison between a preoperative image and a postoperative image.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to
acquire a plurality of first subtraction images in chronological order by respectively subtracting a plurality of contrast images obtained by radiographing a subject into which a contrast media has been injected and a non-contrast image,
acquire, at a radiography time different from a radiography time of the plurality of first subtraction images, a plurality of second subtraction images in chronological order by respectively subtracting a plurality of contrast images obtained by radiographing a subject into which a contrast media has been injected and a non-contrast image,
measure a first profile indicating a change in contrast media concentration over time in a region of interest including a blood vessel in the plurality of first subtraction images,
measure a second profile indicating a change in contrast media concentration over time in a region of interest in the plurality of second subtraction images corresponding to the region of interest in the plurality of first subtraction images,
determine a correction factor on the basis of the first profile and the second profile,
correct at least one of the plurality of first subtraction images and the plurality of second subtraction images on the basis of the correction factor determined, and
control so as to display information based on the plurality of first subtraction images and the plurality of second subtraction images that at least one thereof has been corrected on a display.

2. The X-ray diagnostic apparatus of claim 1, wherein the region of interest is a region including a major artery or capillary vessels which are not affected by treatment.

3. The X-ray diagnostic apparatus of claim 2, wherein the processing circuitry is further configured to detect the major artery in at least one of the plurality of first subtraction images and the plurality of second subtraction images.

4. The X-ray diagnostic apparatus of claim 1, wherein the display is configured to display thereon a perfusion image based on a result of subtraction of the plurality of first subtraction images and the plurality of second subtraction images that at least one thereof has been corrected.

5. The X-ray diagnostic apparatus of claim 1, wherein the processing circuitry is configured to determine at least one of a time lag to arrival of a contrast media, a gain relating to a cardiac output of the subject, and a blood flow velocity so that the first profile and the second profile are approximately matched.

6. The X-ray diagnostic apparatus of claim 1, wherein the plurality of first subtraction images and the plurality of second subtraction images are images of which the radiography times are before and after treatment.

7. The X-ray diagnostic apparatus of claim 1, wherein the processing circuitry is further configured to extract a blood vessel having a largest vessel diameter in blood vessels included within an extraction area set from a lower end to a predetermined position in a subtraction image included in the plurality of first subtraction images or the plurality of second subtraction images, set a plurality of sub regions in the extracted blood vessel, use the plurality of first subtraction images or the plurality of second subtraction images to calculate partial integration value of pixel values for each time with respect to each the sub region, extract a peak value of the partial integration value for each of the sub regions and set a region of which the extracted peak value is lowest as the region of interest.

8. The X-ray diagnostic apparatus of claim 7, wherein the processing circuitry is configured to calculate an X-ray transmittance with respect to each sub region on the basis of a pixel value of the non-contrast image and set a region of which the calculated X-ray transmittance is low not to be the region of interest.

9. The X-ray diagnostic apparatus of claim 1, wherein the processing circuitry is configured to perform a subtraction between the plurality of first subtraction images and the plurality of second subtraction images that at least one thereof has been corrected, calculate a blood-flow-volume difference and a difference degree on the basis of a profile indicating a change in pixel values over time calculated based on the subtraction.

10. The X-ray diagnostic apparatus of claim 1, wherein the processing circuitry is configured to control so as to take the plurality of first subtraction images and the plurality of second subtraction images by matching at least one of an radiography condition, an angle, an FOV (Field of View), an SID (Source to image receptor distance), a position of a collimator, a position of a compensating filter, a size of an X-ray focal point, a beam-hardening filter, a time to injection of contrast media, and an imaging condition between the two subtraction images.

11. The X-ray diagnostic apparatus of claim 1, wherein the processing circuitry is configured to determine the correction factor so that the first profile and the second profile are approximately matched.

12. An X-ray diagnostic apparatus, comprising:
processing circuitry configured to
calculate a plurality of first subtraction images in chronological order by respectively subtracting a non-contrast image little affected by a contrast media from a plurality of contrast images affected by the contrast media on the basis of X-ray dynamic images taken while the contrast media is injecting into a subject,
calculate a plurality of second subtraction images in chronological order by respectively subtracting a non-contrast image little affected by a contrast media from a plurality of contrast images affected by the contrast media on the basis of X-ray dynamic images taken at a radiography time different from a radiography time of the plurality of first subtraction images,
determine misregistration on the basis of two non-contrast images in two X-ray dynamic images,
correct misregistration of at least one of the plurality of first subtraction images and the plurality of second subtraction images on the basis of information on the determined misregistration,
measure a first profile indicating a change in contrast media concentration over time in a region of interest including a blood vessel in the plurality of first subtraction images,
measure a second profile indicating a change in contrast media concentration over time in a region of interest in the plurality of second subtraction images corresponding to the region of interest in the plurality of first subtraction images, determine a correction factor on the basis of the first profile and the second profile, correct at least one of the plurality of first subtraction images and the plurality of second subtraction images on the basis of the correction factor determined, and control so as to display information based on the plurality of first subtraction images and the plurality of second subtraction images that at least one thereof has been corrected on a display.

13. An image processing apparatus, comprising:

processing circuitry configured to obtain a plurality of first subtraction images in chronological order by respectively subtracting a plurality of contrast images obtained by radiographing a subject into which a contrast media has been injected and a non-contrast image, obtain a plurality of second subtraction images in chronological order by respectively subtracting a plurality of contrast images obtained by radiographing a subject into which a contrast media has been injected and a non-contrast image, wherein a radiography time of the plurality of second subtraction images different from a radiography time of the plurality of first subtraction images, measure a first profile indicating a change in contrast media concentration over time in a region of interest including a blood vessel in the plurality of first subtraction images, measure a second profile indicating a change in contrast media concentration over time in a region of interest in the plurality of second subtraction images corresponding to the region of interest in the plurality of first subtraction images, determine a correction factor on the basis of the first profile and the second profile, correct at least one of the plurality of first subtraction images and the plurality of second subtraction images on the basis of the correction factor determined, and control so as to display information based on the plurality of first subtraction images and the plurality of second subtraction images that at least one thereof has been corrected on a display.

14. An image processing apparatus, comprising:

processing circuitry configured to calculate a plurality of first subtraction images in chronological order by respectively subtracting a non-contrast image little affected by a contrast media from a plurality of contrast images affected by the contrast media on the basis of X-ray dynamic images taken while the contrast media is injecting into a subject, calculate a plurality of second subtraction images in chronological order by respectively subtracting a non-contrast image little affected by a contrast media from a plurality of contrast images affected by the contrast media on the basis of X-ray dynamic images taken at a radiography time different from a radiography time of the plurality of first subtraction images, determine misregistration on the basis of two non-contrast images in two X-ray dynamic images, correct misregistration of at least one of the plurality of first subtraction images and the plurality of second subtraction images on the basis of information on the determined misregistration, measure a first profile indicating a change in contrast media concentration over time in a region of interest including a blood vessel in the plurality of first subtraction images, measure a second profile indicating a change in contrast media concentration over time in a region of interest in the plurality of second subtraction images corresponding to the region of interest in the plurality of first subtraction images, determine a correction factor on the basis of the first profile and the second profile, correct at least one of the plurality of first subtraction images and the plurality of second subtraction images on the basis of the correction factor determined, and control so as to display information based on the plurality of first subtraction images and the plurality of second subtraction images that at least one thereof has been corrected on a display.

* * * * *